United States Patent [19]

Thomas et al.

[11] Patent Number: 5,264,613

[45] Date of Patent: Nov. 23, 1993

[54] PROCESS FOR PREPARING ESTER OF HYDROXYMETHYLBENZOCYCLOBUTENES

[75] Inventors: P. J. Thomas; R. Garth Pews, both of Midland, Mich.

[73] Assignee: The Dow Chemical Company, Midland, Mich.

[21] Appl. No.: 861,700

[22] Filed: Apr. 10, 1992

[51] Int. Cl.$^5$ .................. C07C 69/76; C07C 69/34; C07C 313/00

[52] U.S. Cl. .................. 560/85; 560/201; 558/61; 558/214; 558/268

[58] Field of Search .................. 560/201, 85

[56] References Cited

U.S. PATENT DOCUMENTS

| | | |
|---|---|---|
| 2,877,123 | 3/1959 | Rheineck et al. |
| 2,894,983 | 7/1959 | Arnold et al. |
| 2,912,458 | 11/1939 | Brannock |
| 3,288,823 | 1/1962 | Vanderwerff |
| 3,940,434 | 8/1973 | Haas et al. |
| 4,540,763 | 9/1984 | Kirchoff |
| 4,999,449 | 3/1991 | Kirchoff .................. 560/80 |
| 5,204,454 | 4/1993 | Rodenhouse et al. .................. 560/85 |

OTHER PUBLICATIONS

*J. Am. Chem. Soc.*, vol. 96 (1974), pp. 4996–4998, Vollhardt et al., Synthesis of 4-hydroxymethylbenzocyclobutene by a cyclization process.
vol. 71 (1949), pp. 122–125, Chaikin et al, Reduction of Aldehydes, Ketones and Acid Chlorides by Sodium Borohydride.

*Primary Examiner*—José G. Dees
*Assistant Examiner*—Dwayne C. Jones

*Attorney, Agent, or Firm*—Charlotte M. Kraebel; Charles J. Enright

[57] ABSTRACT

A process for preparing carboxylic acid esters of of the formula $$X-(COOCH_2A)_n$$

wherein A is the residue of a substituted or unsubstituted 3- or 4-benzocyclobutene compound, X is an n-valent organic bridging group, and n is 2,3, or 4, comprises reacting a substituted or unsubstituted 3- or 4-hydroxymethylbenzocyclobutene compound with a compound of the formula $X-(COY)_n$, wherein X is an n-valent organic bridging group and Y is Cl or Br. Esters of inorganic acids of the formula $$X'(OCH_2A)_n$$

wherein X' is a residue of an inorganic acid halide, n is 2 or 3, and A is the residue of a substituted or unsubstituted 3- or 4-benzocyclobutene compound, are prepared by reacting an inorganic halide of the formula $X'Y_n$, wherein Y is Br or Cl, with a substituted or unsubstituted 3- or 4-hydroxymethylbenzocyclobutene compound. Biscarbonates of the formula $X''[OC(=O)CH_2A]_2$ wherein $X''$ is the residue of a diphenol are prepared by reaction between a bis(halocarbonyl) compound of the formula $X''[OC(=O)Y]_2$, wherein Y is Cl or Br, and a substituted or unsubstituted 3- or 4-hydroxymethylbenzocyclobutene compound. The resulting esters are useful for making resins.

7 Claims, No Drawings

PROCESS FOR PREPARING ESTER OF HYDROXYMETHYLBENZOCYCLOBUTENES

DESCRIPTION

1. Technical Field

This invention relates to low a temperature, high yield process for preparing esters of hydroxyalkylbenzocyclobutenes, particularly hydroxymethylbenzocyclobutene. The esters are useful as intermediates for producing specialty polymers. A low temperature process for preparing these intermediates is highly important, because benzocyclobutenes tend to polymerize through ring opening in orthoxylylene moieties at high temparatures.

2. Background Art

Kirchhoff, U.S. Pat. No. 4,540,763, herein incorporated by reference recites the preparation of polymers, derived from poly(arylcyclobutenes), most of which are derived from phenols. Kirchhoff (U.S. Pat. No. 4,999,449), herein incorporated by reference, recites the preparation of bridged arylcyclobutene compounds.

Arnold et al. (U.S. Pat. No. 2,894,983) have disclosed the preparation of succinic acid esters from endomethylene-delta$^3$-tetrahydrophenylethanol or similar alcohols by reaction with succinic anhydride.

Brannock (U.S. Pat. No. 2,912,458) discloses the synthesis of bis-(2-methyl-2-norcamphanemethanol)alkanedioates, prepared by esterification with a saturated dicarboxylic acid.

Haas et al. (U.S. Pat. No. 3,940,434) have proposed the preparation of benzocycloalkene derivatives, substituted in the 1-position by ester groups.

Vollhardt et al., J. Am. Chem. Soc., vol. 96 (1974), pp. 4996–4998, have disclosed the synthesis of 4-hydroxymethylbenzocyclobutene by a cyclization process, which gives a 14% yield of the desired product.

An improved process for the synthesis of hydroxyalkylbenzocyclobutenes from formyl or ketobenzocyclobutenes is disclosed in our copending patent application, Ser. No. 07/861,693, filed on Apr. 1, 1992.

DISCLOSURE OF THE INVENTION

In one aspect, this invention relates to a process for preparing carboxylic acid esters of the formula X—(COOCH$_2$A)$_n$ wherein A is the residue of a substituted or unsubstituted 3- or 4-benzocyclobutene compound, X is an n-valent organic bridging group, and n is 2, 3, or 4, which comprises reacting a substituted or unsubstituted 3- or 4-hydroxymethylbenzocyclobutene compound with a compound of the formula X—(COY)$_n$, wherein X is an n-valent organic bridging group and Y is Cl or Br.

This invention further relates to a process for preparing esters of inorganic acids of the formula X'(OCH$_2$A)$_n$ wherein X' is a residue of an inorganic acid halide, n is 2 or 3, and A is the residue of a substituted or unsubstituted 3- or 4-benzocyclobutene compound by reacting an inorganic halide of the formula X'Y$_n$, wherein Y is Br or Cl, with a substituted or unsubstituted 3- or 4-hydroxymethylbenzocyclobutene compound.

In a further aspect, this invention relates to a process for preparing carbonate esters of the formula

X"[OC(=O)OCH$_2$A]$_2$ wherein X" is the residue of a diphenol and A is the residue of a substituted or unsubstituted 3- or 4-benzocyclobutene compound, comprising reacting a bis(-halocarbonyl) compound of the formula X"[OC(=O)Y]$_2$, wherein Y is Cl or Br, with a substituted or unsubstituted 3- or 4-hydroxymethylbenzocyclobutene compound.

This invention further relates to difunctional or polyfunctional esters, prepared by the foregoing process.

The process for preparing the esters is carried out at a temperature below that at which dimerization or oligomerization of the hydroxyalkylbenzocyclobutene starting material or ester is a significant side reaction, for a time sufficient to convert the hydroxymethylbenzocyclobutene compound to the ester.

"Benzocyclobutene," as used in the specification and claims, includes carbocyclic and heterocyclic arylcyclobutene (cyclobutene (cyclobutarene) compounds, which consist of a cyclobutene ring fused to an aromatic carbocyclic or heterocyclic ring. Aromatic as used herein refers to carbocyclic or heterocyclic rings in which 4n+2 delocalized pi electrons are contained in an orbital ring. This property is also known as resonance stabilization or delocalization.

Preferred carbocyclic aromatic moieties include benzene, naphthalene, phenanthrene, anthracene, a biaryl moiety of two or more aromatic radicals, bridged by alkylene or cycloalkylene moieties. More preferred carbocyclic aromatic radicals include benzene, napthtalene, biphenyl, binaphthyl, diphenylalkane or diphenylcycloalkane radicals. The most preferred carboxylic aromatic radical is a benzene radical, which, when fused to a cyclobutene ring, produces the simplest member of the series, benzocyclobutene.

Examples of preferred heterocyclic aromatic compounds include pyrrole, furan, thiophene, imidazole, oxazole, thiazole, pyrazine, pyridine and pyrimidine. More preferred heterocyclic aromatic radicals are pyridine, furan and thiophene, with cyclobutapyridine being most preferred. The carbocyclic analogs are preferred over the heterocyclic analogs.

Either the aryl radical or the cyclobutene ring can be substituted by electron-donating or electron-withdrawing groups, provided that the substituent is not reduced by the sodium borohydride. Examples of such substituents include cyano, halo, carboxy, hydrocarbyloxy, alkylsulfonyl, alkylsulfonyl, amido, alkyl, alkenyl or aryl groups.

It will be understood that "benzocyclobutene" is an art-recognized term. In the commonly-used non-systematic numbering system for benzocyclobutenes, the 1-and 2-positions are in the cyclobutene ring. The 3- and 6-positions are in an aromatic ring, adjacent to the cyclobutene ring. The 4- and 5-positions are metato the cyclobutene ring. The simplest member of the series, benzocyclobutene, is formally identified as bicyclo[4.2.-0]octa-1,3,5-triene. A compound, formally identified as 3-hydroxymethylbicyclo[4.2.0]octa-1,3,5-triene, is commonly known as 4-hydroxymethylbenzocyclobutene. The common names will be used in the specification and claims.

The ester products of this invention are a type of bridged benzocyclobutene, characterized for the sake of simplicity as hydroxymethylbenzocyclobutene derivatives of the formula

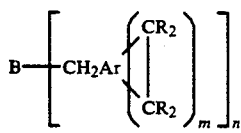

wherein B is an n-valent bridging moiety containing oxygen, bonded to the aromatic ring (Ar) of the benzocyclobutene unit by an intervening methylene moiety, m is an integer of 1 or more, n is an integer of 2 or more and each R is hydrogen or an electron-donating or electron-withdrawing substituent.

In the simplest cases, the cyclobutene ring is unsubstituted (each R is H and m is 1) and the aromatic ring is benzene. This case can be represented by the subgeneric formula

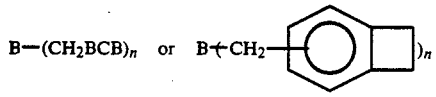

wherein B is the oxygen-containing bridging function and n is as above. In this formula, BCB represents 3- or 4-benzocyclobutenyl.

Representative oxygen-containing bridging groups include, but are not limited to, —O(C=O)NH—, —O(C=O)O—, —O—, —O—Q—O—, —O(C=O)—Q—(C=O)O—, —O—(C=O)— or —O(C=O)—O—Q—O(C=O)O— wherein Q is a divalent bridging group, such as phenylene, xylylene, tolylene, arylene-alkylene-arylene, alpha, omega-alkylene and the like.

Preferred bridging groups in accordance with this invention include ester carboxylic acid groups, such as terephthaloyloxy or adipoyloxy, which produce bridged derivatives of the formulas

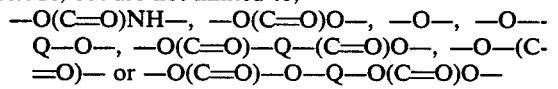

or

BCBCH₂—O(C=O)—(CH₂)₆(C=O)O—CH₂BCB, respectively.

Another particularly preferred bridging group is the carbonate group. In the simplest case, the product is of the formula

BCBCH₂—O—(C=O)—O—CH₂BCB.

Other preferred carbonate esters are those corresponding to the formula

X''[OC(=O)OCH₂A]₂ wherein X'' is the residue of a diphenol and A is the residue of a substituted 3- or 4-benzocyclobutene compound.

Exemplary hydroxymethylbenzocyclobutene compounds which can be converted to esters in accordance with this invention include, but are not limited to, compounds of the structures:

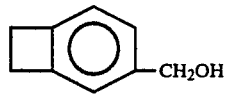

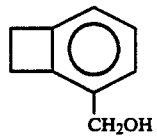

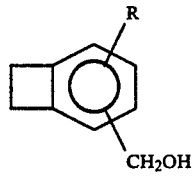

wherein R is alkyl, vinyl, substituted vinyl, ethinyl, substituted ethinyl, aryl, polyaryl, substituted aryl, substituted polyaryl, heterocyclic, heteroaryl, alkylaryl, alkylheterocyclic, arylheteroaryl, trialkysilyl, nitro, cyanato, benzobicyclobutenyl, alkylbenzocyclobutenyl, arylbenzocyclobutenyl, alkylarylbenzocyclobutenyl, arylalkylbenzocyclobutenyl, oxybenzocyclobutenyl, thiobenzocyclobutenyl, benzocyclobutenyl sulfonyl, benzocyclobutenyl sulfoxide, carboxy, mono or dialkylamino, mono or diarylamino, mono or diheterocyclic amino, mono or diheteroaryl amino, hydroxyl, alkoxy, aryloxy, substituted alkoxy, substituted aryloxy, polyaryloxy, substituted polyaryloxy, mercapto, alkylthio, substituted alkylthio, arylthio, substituted arylthio, polyarylthio, substituted polyarylthio, heterocyclothio and heteroarylthio. Substituted compounds include hydrocarbyl substituents, as recited by Kirchhoff, supra.

Representative higher fused ring benzocyclobutene reactants include, but are not limited to, compounds of the formulas:

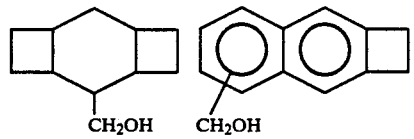

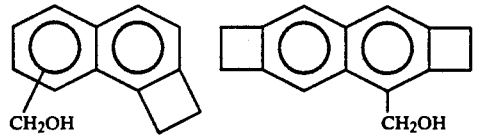

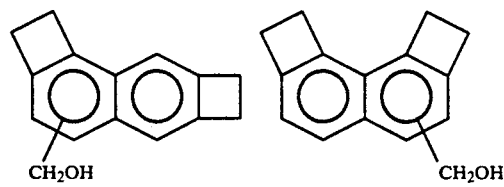

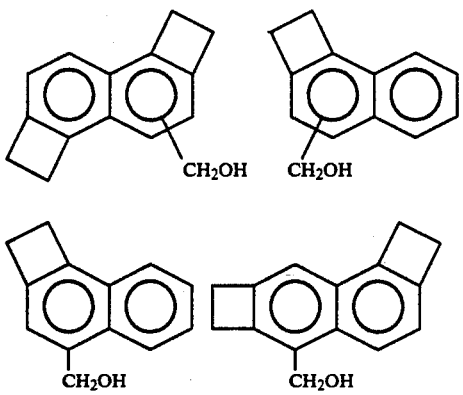

It will be understood that the fused ring benzocyclobutenes can be substituted as above and that bis(hydroxyalkyl) or bis(hydroxymethyl) compounds can also be used. For the sake of simplicity, it is preferred to use hydroxymethylbenzocyclobutene starting materials.

Preferred reactants for the practice of this invention are those containing 3- or 4-hydroxymethylbenzocyclobutene moiety, more preferably a 4-hydroxymethylbenzocyclobutene moiety. The most preferred benzocyclobutene reactant is 4-hydroxymethylbenzocyclobutene.

4-Formylbenzocyclobutene, used to make 4-hydroxymethylbenzocyclobutene, is a known compound, the synthesis of which is recited by Wong et al., U.S. Pat. No. 4,708,990, herein incorporated by reference. Applicants' preferred process for preparing hydroxyalkylbenzocyclobutene compounds employs sodium borohydride as set forth in more detail in the Examples.

In the preparation of carboxylic acid esters in accordance with this invention, carboxylic acid halides of the formula X—(COY)$_n$ can be selected from di-, tri- and tetra-halides of corresponding di-, tri-and tetracarboxylic acids, including aliphatic, aromatic and heterocyclic acids. Preferred carboxylic acid halides include, but are not limited to, isophthaloyl dichloride, terephthaloyl dichloride, phthaloyl dichloride, adipoyl chloride, succinoyl chloride, dodecanoyl chloride, methylsuccinoyl chloride, 1,3,5-tris(chlorocarbonyl)benzene, tetrakis(chlorocarbonyl)benzene or the like. Preferred carboxylic acid halides are isophthaloyl chloride, succinoyl chloride and p-biphenyldicarboxylic acid dichloride.

Preferred carboxylic acid esters in accordance with this invention are, therefore, those represented by the formulae

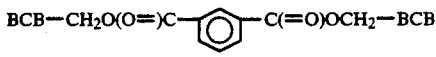

or

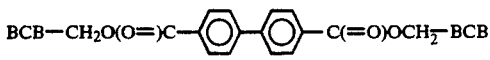

wherein BCB is 4-benzoyclobutenyl.

Esters of inorganic acids are prepared from ahlides of the formula X'Y$_n$, wherein X' is a residue of an inorganic acid halide, n is 2 or 3, and Y is Br or Cl. Typical inorganic acid halides include phosgene (X' is C=O), carbonyl bromide, thionyl chloride (X' is S=O), sulfuryl chloride (X' is SO$_2$), phosphorus trichloride (X' is P), phosphorus oxychloride (X' is P=O), phosphorus oxybromide or the like. More preferably, the inorganic acid chloride is phosgene, thionyl chloride or phosphorus oxychloride. Most preferred esters, corresponding to bis(benzocyclobutenyl) carbonates, are prepared from phosgene and a substituted or unsubstituted 3- or 4-hydroxymethylbenzocyclobutene compound.

Organic carbonate esters can be prepared from bis(halocarbonyloxy)aromatic compounds, obtained by treating precursor diphenolic compounds with phosgene or carbonyl bromide. The reaction can be represented, in the case of phosgene, by the equation:

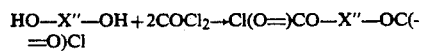

wherein X'' is the residue of a diphenol. Diphenols which can be used include, for example, resorcinol, hydroquinone, bisphenol A and bisphenol F.

The bis(halocarbonyloxy)aromatic compounds, for example, Cl(O=)CO—X''—OC(=O)Cl, react with hydromethylbenzocyclobutene compounds to produce corresponding biscarbonate esters. Most preferably, the bis(halocarbonyloxy)aromatic compound is bis(chlorocarbonyl)bisphenol A, which is reacted with 4-hydroxymethyl benzocyclobutene to produce a biscarbonate ester.

In the case of bis(chlorocarbonyl)hydroquinone and 4-hydroxymethylbenzocyclobutene, the reaction can be represented by the equation:

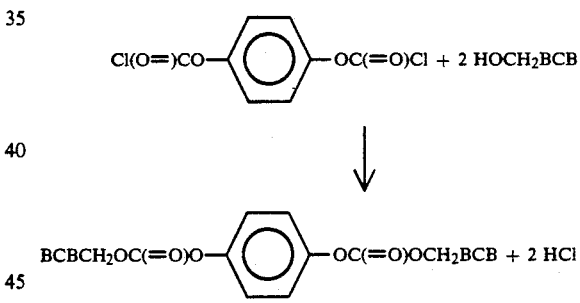

The esterifications are carried out in a solvent, which is selected for being inert to the acid halide being used. Solvents are accordingly selected from esters, ketones, ethers, nitriles or halogenated hydrocarbons. Preferred solvents include ethyl acetate, isopropyl acetate, methyl ethyl ketone, acetone, ethylene glycol dimethyl ether, tetrahydrofuran or the like.

The ratio of hydroxymethylbenzocyclobutene compound to dicarboxylic acid dihalide is between 2:1 to 2.2:1. More preferably, the ratio is from about 2:1 to 2.1:1, on a molar basis.

The reaction is done in the presence of a hydrogen halide acceptor, which can be selected from organic or inorganic hydrogen halide acceptors.

Organic hydrogen halide acceptors, used in the practice of this invention, are tertiary amines. Representative organic hydrogen halide acceptors include, but are not limited to, trimethylamine, triethylamine, diethyl-n-butylamine, triisobutylamine, tri-n-butylamine, triisopropylamine, N,N,N',N'-tetramethylethylene diamine, N,N-dimethylcyclohexylamine, N,N-diethylcyclohexylamine, N,N-diethylaniline, N,N-dimethylaniline, N-methyltoluidine, pyridine, quinoline, the lutidines, N-methylpiperidine, N-methylpyrrole and the like.

Preferred organic hydrogen halide acceptors are tertiary amines, particularly heterocyclic tertiary amines, such as pyridine or lutidine, or those represented by the formula $R_1R_2R_3N$, wherein each of $R_1$, $R_2$ and $R_3$ is selected independently from straight-chain and branched-chain alkyl of 1-8 carbon atoms and cycloalkyl. Most preferably, the organic hydrogen halide acceptor is pyridine.

Inorganic hydrogen halide acceptors are selected from salts of weak acids and strong bases or corresponding oxides or hydroxides, particularly of the Group I alkali metals and Group II alkaline earth metals. Inorganic hydrogen halide acceptors accordingly include salts, oxides and hydroxides of lithium, sodium, potassium, cesium, magnesium, calcium, strontium and barium.

Preferred inorganic hydrogen halide acceptors are selected from alkali metal hydroxides, carbonates, and acylates, particularly acetates or propionates. Most preferred are sodium or potassium acetate.

The ratio of hydrogen halide acceptor to acid halide can be varied from about 2:1 to about 10:1, on an equivalency basis. Using greater excesses of hydrogen halide acceptor is not particularly advantageous. It has been found that excellent results are obtained using 2-3 equivalents of hydrogen halide acceptor per equivalent of acid chloride. Therefore, preferred ratios of hydrogen halide acceptor to acid halide are from about 2:1 to about 2.7:1 equivalents.

The esterifications can be carried out at room temperature. If it is found that a reaction using a given starting material is highly exothermic, the reaction mixture can be cooled with an ice bath.

At the end of the reaction, solvent is removed. The dry residue is taken up in water and extracted into an organic solvent, e.g. ethyl acetate. The ethyl acetate solution is washed with water and brine and dried over an anhydrous salt. 4-Hydroxymethylbenzocyclobutene esters can be recrystallized from hot hexanes.

The process of converting hydroxymethylbenzocyclobutenes to esters is particularly advantageous because the low reaction temperature results in a very low degree of oligomerization or polymerization. The yields of ester often exceed 75-80%.

The process of this invention can be carried out in any container, with or without a stirring attachment, which is not attacked by the reactants, or products of the invention.

Cyclobutapyridines can be prepared by the pyrolysis of 4-pyridyl propargyl ether at 550° C. See J. M. Riemann et al., *Tetrahedron Letters*, no. 22 (1977), pages 1867-1870. Alternatively, a pyridine-4-carbonitrile, having an alkyl substituent on the carbon atom adjacent to the nitrile, is reacted with sodium azide and ammonium chloride in N,N-dimethylformamide to prepare a 5-(alkyl-4-pyridyl)tetrazole. The 5-(alkyl-4-pyridyl)tetrazole is pyrolyzed at about 600° C. to a cyclobutapyridine. See W. D. Crow et al., *Austrailian Journal of Chemistry* (1975), after page 1741. 2-Bromocyclobuta[b]pyridine can be prepared from 2-hydroxy[b]cyclobutapyridine. See Kirchhoff et al., U.S. Pat. No. 4,783,514, herein incorporated by reference.

BEST MODE FOR CARRYING OUT THE INVENTION

Most preferably, the esters made by the process are those made by reaction between 4-hydroxymethylbenzocyclobutene and isophthaloyl chloride, succinoyl chloride or biphenyldicarboxylic acid dichloride.

Without further elaboration it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the following examples, the temperatures are set forth uncorrected in degrees Celsuis. Unless otherwise indicated, all parts and percentages are by weight.

EXAMPLE 1

To a stirred solution of 1.32 g of 4-formylbenzocyclobutene in 15 mL of ethanol at room temperature is added 0.38 g of sodium borohydride. The reaction mixture is stirred for 2 h at room temperature. Ethanol is removed using a rotary evaporator and the residual material is diluted with 50 mL of water.

The aqueous mixture is extracted with ethyl acetate. The ethyl acetate layer is washed with water and with saturated sodium chloride brine and dried over anhydrous magesium sulfate. The solution is filtered and solvent is removed from the filtrate. The yield of 4-hydroxymethylbenzocyclobutene is 1.27 g (95%, m.p. 70° C. from hexanes).

EXAMPLE 2

1-Formylbenzocyclobutene is reduced with sodium borohydride in water, containing 1% by weight of sodium hydroxide. 4-Hydroxymethylbenzocyclobutene is obtained.

EXAMPLE 3

4-Formylbenzocyclobutene is reduced with sodium borohydride in tetrahydrofurfuryl alcohol solvent. Similar results are obtained.

EXAMPLE 4

Esterification of Hydroxymethylbenzocyclobutene

To a stirred solution of 37.3 mmol of hydroxymethylbenzocyclobutene in 25 mL of methylene chloride at room temperature under a nitrogen atmosphere are added 4 mL of pyridine, 50 mg of dimethylaminopyridine and 18.6 mmol of acid chloride. The reaction mixture is stirred for 6 h at room temperature. The reaction mixture is poured into water and extracted with ethyl acetate.

The organic extract is washed with cold dilute hydrochloric acid, with water, with sodium bicarbonate solution and with saturated sodium chloride brine and dried over anhydrous magnesium sulfate. After removing solvent, the residue is recrystallized. Yields are 70-80%.

(a) Bisester from isophthaloyl chloride: m.p. 73° C. (from hexanes, ethyl acetate)
(b) Bisester from succinoyl chloride: m.p. 51° C. (from hexanes)
(c) Bisester from biphenyldicarboxylic acid dichloride [p—Cl(O=)C—C$_6$H$_4$—C$_6$H$_4$C(=O)Cl—p]: reaction run in tetrahydrofuran, m.p. 141° C. (from ethyl acetate)

Similar reactions are done using the following diacid halides:

(d) adipoyl chloride
(e) phosgene
(f) terephthaloyl chloride
(g) phosphorus oxychloride
(h) thionyl chloride
(i) bis(chlorocarbonyl)resorcinol m—Cl(O=)COC$_6$H$_4$OC(=O)Cl
(j) bis(chlorocarbonyl)bisphenol A p—Cl(O=)COC$_6$H$_4$C(CH$_3$)$_2$C$_6$H$_4$OC(=O)Cl—p (k) 1,3,5-tris(chlorocarbonyl)benzene 1,3,5—C$_6$H$_3$(COCl)$_3$
(l) tetrakis(chlorocarbonyl)benzene C$_6$H$_2$(COCl)$_4$ Similar results are obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A process for preparing a carboxylic acid ester of the formula

X—(COOCH$_2$A)$_n$ wherein A is the residue of the substituted or unsubstituted 3- or 4-hydroxymethylbenzocyclobutene compound, and n is 2, 3, or 4, comprising reacting a substituted or unsubstituted 3- or 4-hydroxymethylbenzocyclobutene compound with a compound of the formula X—(COY)$_n$, wherein X is an n-valent organic bridging group derived from the corresponding di, tri and tetra carboxylic acids and Y is Cl or Br.

2. The process of claim 1, wherein n is 2 and Y is Cl.
3. The process of claim 1, wherein A is 4-benzocyclobutenyl.
4. The process of claim 1, wherein n is 2, Y is Cl and A is 4-benzocyclobutenyl.
5. The process of claim 1, carried out in the presence of a hydrogen halide acceptor.
6. The process of claim 1, wherein X—(COY)$_n$ is isophthaloyl chloride and A is 4-benzocyclobutenyl.
7. The process of claim 1, wherein X—(COY)$_n$ is p—Cl(O=)C—C$_6$H$_4$—C$_6$H$_4$C(=O)Cl—p and A is 4-benzocyclobutenyl.

* * * * *